(12) United States Patent
Nagao et al.

(10) Patent No.: US 9,649,401 B2
(45) Date of Patent: May 16, 2017

(54) ULTRAVIOLET IRRADIATION APPARATUS

(71) Applicant: Panasonic Intellectual Property Management Co., Ltd., Osaka (JP)

(72) Inventors: Nobuaki Nagao, Gifu (JP); Takehiro Zukawa, Osaka (JP); Yoshiki Sasaki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/150,077

(22) Filed: May 9, 2016

(65) Prior Publication Data

US 2016/0339138 A1    Nov. 24, 2016

(30) Foreign Application Priority Data

May 18, 2015    (JP) .................................. 2015-101326

(51) Int. Cl.
| | | |
|---|---|---|
| *A61L 12/06* | (2006.01) | |
| *A61L 2/10* | (2006.01) | |
| *C02F 1/32* | (2006.01) | |

(52) U.S. Cl.
CPC ............... *A61L 12/063* (2013.01); *A61L 2/10* (2013.01); *C02F 1/32* (2013.01)

(58) Field of Classification Search
CPC ............. A61L 12/063; A61L 2/10; C02F 1/32
See application file for complete search history.

(56) References Cited

U.S. PATENT DOCUMENTS

| | | | |
|---|---|---|---|
| 2002/0089275 A1* | 7/2002 | Falkenstein | A61L 2/10 313/29 |
| 2003/0030374 A1* | 2/2003 | Pai | A61L 2/14 313/582 |
| 2006/0195166 A1 | 8/2006 | Minamoto et al. | |
| 2012/0039747 A1* | 2/2012 | Morfill | A61L 2/14 422/22 |
| 2012/0121470 A1* | 5/2012 | Morito | A61L 9/205 422/121 |

(Continued)

FOREIGN PATENT DOCUMENTS

| | | |
|---|---|---|
| JP | 55-157378 | 12/1980 |
| JP | 11-155943 | 6/1999 |

(Continued)

*Primary Examiner* — Nicole Ippolito
*Assistant Examiner* — Sean Luck
(74) *Attorney, Agent, or Firm* — McDermott Will & Emery LLP

(57) ABSTRACT

An ultraviolet irradiation apparatus includes: a first substrate; a second substrate; electrodes disposed directly or indirectly on the first substrate; a dielectric layer covering the electrodes; a sealant joining together the first and second substrates; a light-emitting layer that is disposed directly or indirectly on the dielectric layer and/or a surface of the second substrate; and a reaction vessel disposed directly or indirectly on a surface of the second substrate. The reaction vessel includes a tubular structure, an inlet channel and an outlet channel. The tubular structure has a ratio ha/hc of 5 to 10, where ha is a diameter of a circle inscribed in an inner bottom surface of the tubular structure, and hc is an inner height of the tubular structure.

8 Claims, 12 Drawing Sheets

(56) References Cited

U.S. PATENT DOCUMENTS

| | | | | |
|---|---|---|---|---|
| 2012/0213664 A1* | 8/2012 | Diver | ............... | H05H 1/2406 |
| | | | | 422/22 |
| 2013/0216431 A1* | 8/2013 | Halfmann | ............. | A61L 2/10 |
| | | | | 422/24 |
| 2013/0221236 A1* | 8/2013 | Mastenbroek | ........ | H01J 65/046 |
| | | | | 250/435 |

FOREIGN PATENT DOCUMENTS

| | | |
|---|---|---|
| JP | 2005-201586 | 7/2005 |
| JP | 2006-087472 | 4/2006 |
| JP | 2010-080440 | 4/2010 |
| JP | 2012-146712 | 8/2012 |
| JP | 2012-236948 | 12/2012 |
| JP | 2014-076422 | 5/2014 |

\* cited by examiner

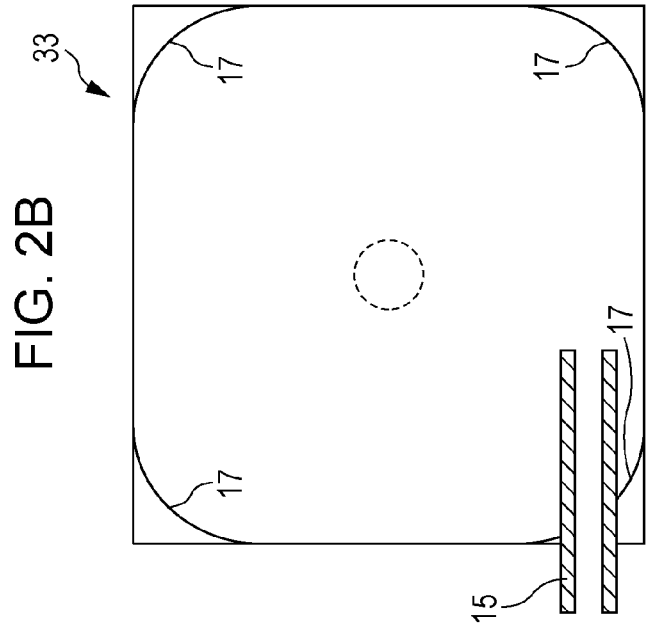
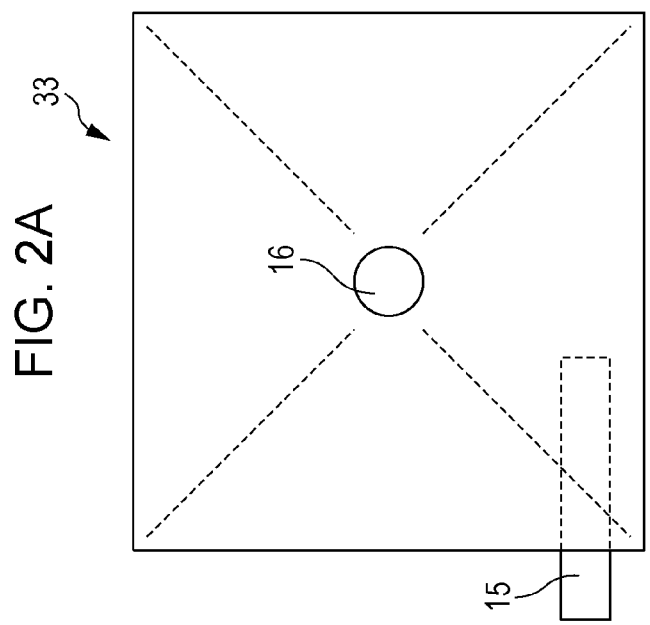

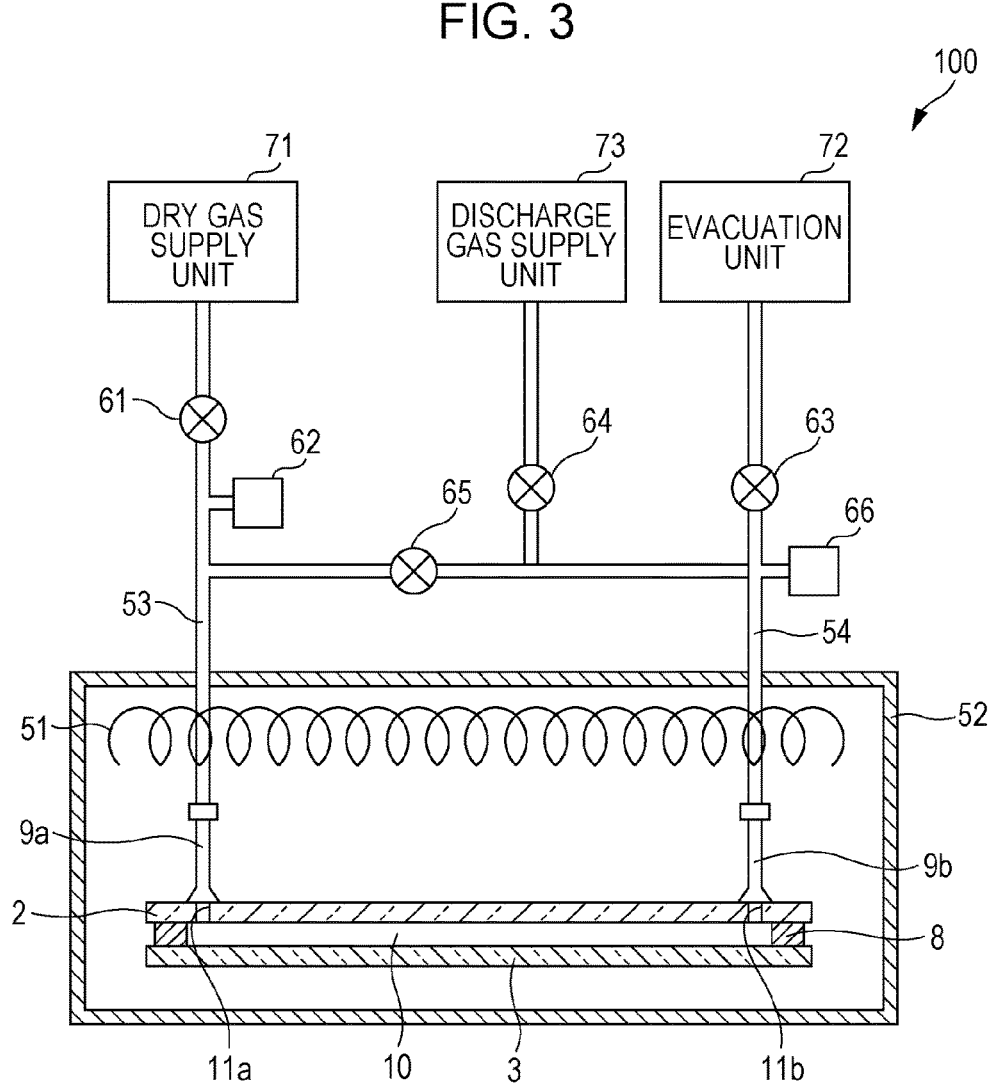

ULTRAVIOLET IRRADIATION APPARATUS

BACKGROUND

1. Technical Field

The present disclosure relates to ultraviolet irradiation apparatuses, and particularly to ultraviolet irradiation apparatuses for irradiating fluids with ultraviolet light.

2. Description of the Related Art

Ultraviolet light (ultraviolet radiation), particularly deep-ultraviolet light (deep-ultraviolet radiation), which has wavelengths of about 200 to 350 nm, is used in a variety of fields such as sterilization, deodorization, cleaning, water purification, lithography, and illumination for its ability to decompose organic substances.

Mercury lamps, which cause a glow discharge of mercury, are widely used as ultraviolet light sources (see, for example, Japanese Unexamined Patent Application Publication No. 2012-146712). Japanese Unexamined Patent Application Publication No. 2012-146712 teaches the use of deep-ultraviolet light with a wavelength of 254 nm emitted from a mercury lamp to efficiently decompose and remove carbon contaminants deposited on a mask or other component used in an exposure apparatus without damaging its optical system.

SUMMARY

One non-limiting and exemplary embodiment provides an ultraviolet irradiation apparatus that can efficiently irradiate a fluid with ultraviolet light.

In one general aspect, an ultraviolet irradiation apparatus includes: a first substrate having a main surface; a second substrate facing the main surface of the first substrate and comprising a material that transmits ultraviolet light; electrodes disposed directly or indirectly on the main surface of the first substrate; a dielectric layer covering the electrodes; a sealant joining together the first and second substrates to form a sealed discharge space between the first and second substrates; a light-emitting layer that is disposed directly or indirectly on the dielectric layer and/or a surface of the second substrate facing the discharge space and that receives excitation light generated in the discharge space and emits ultraviolet light; and a reaction vessel disposed directly or indirectly on a surface of the second substrate facing away from the discharge space. The reaction vessel includes a tubular structure, an inlet channel that directs a fluid flowing from outside the reaction vessel into the tubular structure, and an outlet channel that directs the fluid flowing from inside the tubular structure out of the reaction vessel. The tubular structure having a ratio ha/hc of 5 to 10, where ha is a diameter of a circle inscribed in an inner bottom surface of the tubular structure, and hc is an inner height of the tubular structure.

According to the present disclosure, an ultraviolet irradiation apparatus that can efficiently irradiate a fluid with ultraviolet light can be provided.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIGS. 2A and 2B illustrate the construction of a cyclone structure shown in FIG. 1;

FIG. 3 is a schematic view illustrating the construction of a sealing/evacuation oven for the manufacture of a deep-ultraviolet light-emitting device shown in FIG. 1;

DETAILED DESCRIPTION

Underlying Knowledge Forming Basis of the Present Disclosure

The underlying knowledge forming the basis of the present disclosure will be described first. To reduce environmental impacts, regulations on environmentally hazardous substances such as mercury, including the WEEE and RoHS Directives in Europe, are becoming increasingly restrictive. It would thus be desirable to develop an ultraviolet light source that could replace mercury lamps.

Figure 8:
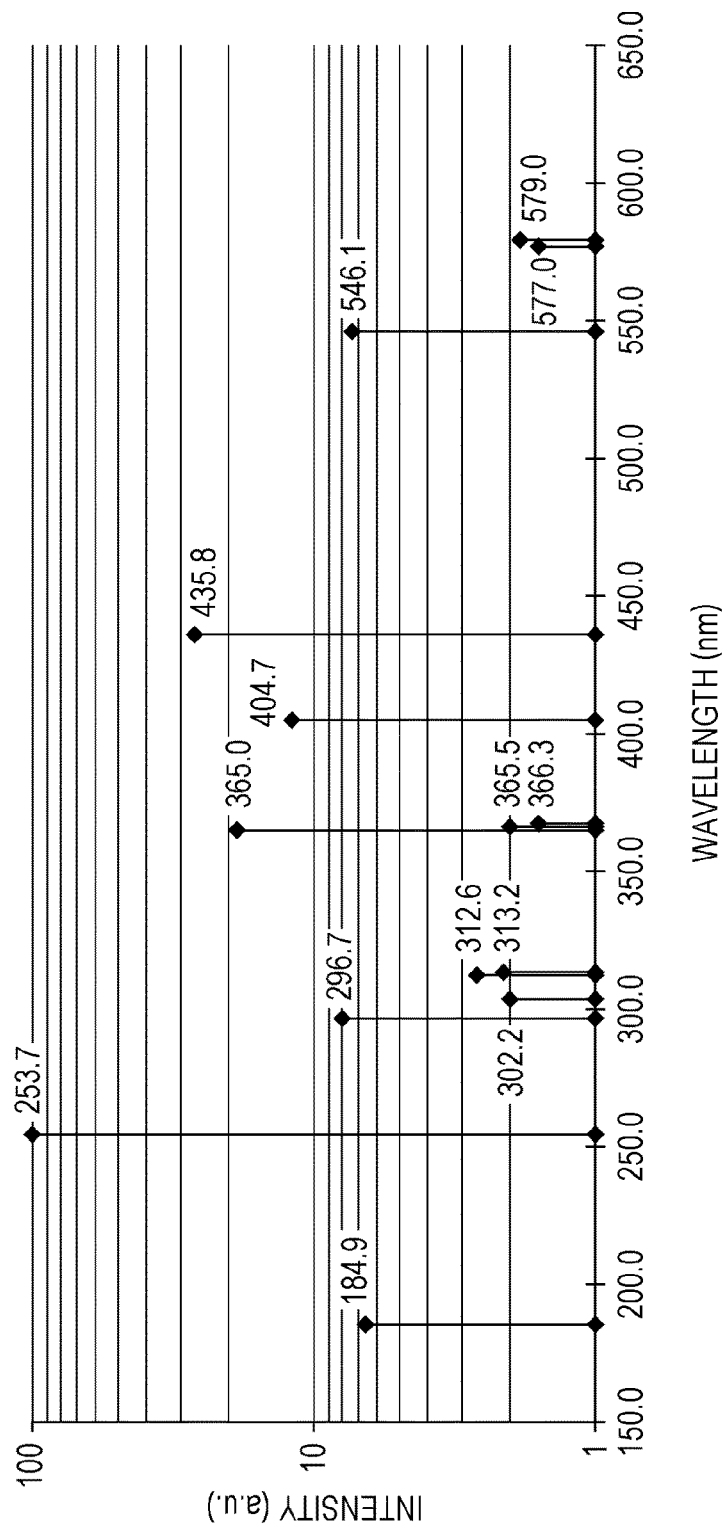
FIG. 8 is a graph showing the emission spectrum of a mercury lamp.

FIG. 8 shows the emission spectrum of a mercury lamp. As can be seen from FIG. 8, the emission spectrum of a mercury lamp shows a peak near 185 nm, which contributes to the generation of ozone. Ultraviolet irradiation apparatuses including mercury lamps utilize the sterilization and decomposition effect of both ozone and ultraviolet light. One approach to reduce the generation of ozone is to reduce the output of mercury lamps; however, this approach is disadvantageous in that it sacrifices the sterilization and decomposition capability of ultraviolet light.

Another problem with ultraviolet irradiation apparatuses known in the art is that they cannot efficiently irradiate a fluid with ultraviolet light. It is often the case that an ultraviolet irradiation apparatus is difficult to install in a channel for a fluid to be irradiated with ultraviolet light. Even if the ultraviolet irradiation apparatus can be installed in the channel, it is often difficult to ensure that the fluid is uniformly irradiated with ultraviolet light for the required period of time.

Ultraviolet irradiation apparatuses according to non-limiting and exemplary embodiments will now be described with reference to the drawings. It should be noted that the embodiments described below are desirable general or specific embodiments of the present disclosure. The values, shapes, materials, elements, arrangements and manners of connection of elements, steps, step sequences, and other features illustrated in the following embodiments are for illustration purposes only and are not intended to limit the present disclosure. Among the elements illustrated in the following embodiments, those not disclosed in the independent claim representing the broadest concept are illustrated as optional elements that constitute desirable embodiments. Same or similar elements in different figures are indicated by same numerals to avoid duplication of description.

First Embodiment

Figure 1:
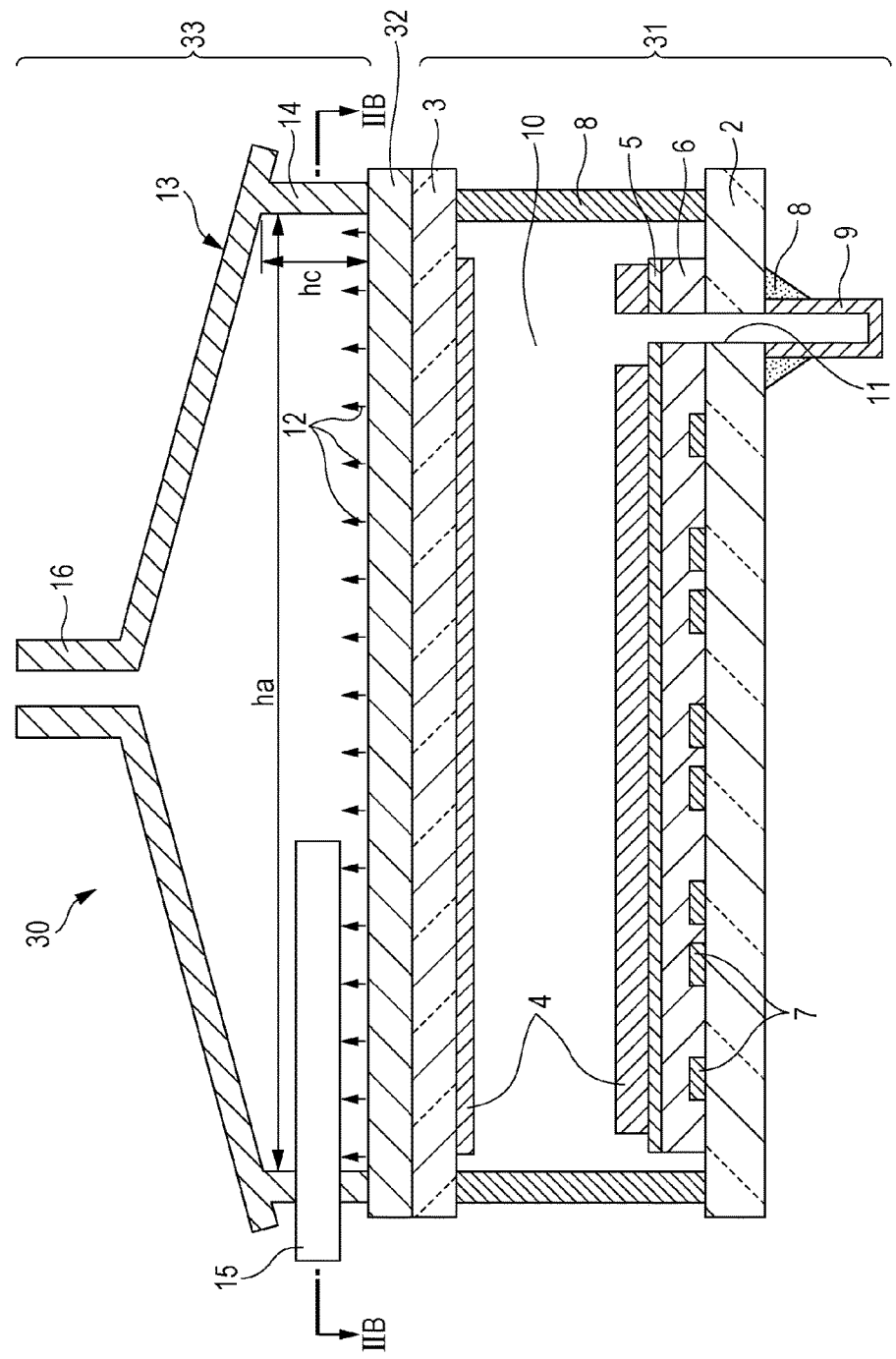
FIG. 1 is a schematic sectional view illustrating the construction of an ultraviolet irradiation apparatus according to a first embodiment.

FIG. 1 is a schematic sectional view illustrating the construction of an ultraviolet irradiation apparatus 30 according to a first embodiment. The ultraviolet irradiation apparatus 30 irradiates a fluid (i.e. liquid or gas) with ultraviolet light (e.g. deep-ultraviolet light) 12. The ultraviolet irradiation apparatus 30 includes a deep-ultraviolet light-emitting device 31, an ultraviolet light filter 32 disposed on the deep-ultraviolet light-emitting device 31, and a cyclone structure 33 disposed on the ultraviolet light filter 32.

The deep-ultraviolet light-emitting device 31 emits ultraviolet light (particularly, deep-ultraviolet light) upward (i.e., toward the ultraviolet light filter 32 and the cyclone structure 33). The deep-ultraviolet light-emitting device 31 includes, as main elements, a first substrate 2, electrodes 7 disposed on a main surface of the first substrate 2, a dielectric layer 6 covering the electrodes 7, a second substrate 3 facing the main surface of the first substrate 2 and containing a material that transmits ultraviolet light, and a sealant 8 joining together the first and second substrates 2 and 3 to form a sealed discharge space 10 between the first and second substrates 2 and 3. The deep-ultraviolet light-emitting device 31 also includes a light-emitting layer 4 disposed on the surface of the dielectric layer 6 facing the discharge space 10 and/or on the surface of the second substrate 3 facing the discharge space 10. The light-emitting layer 4 emits ultraviolet light in response to excitation light generated in the discharge space 10.

The ultraviolet light filter 32 is disposed between the second substrate 3 and the cyclone structure 33 and absorbs or reflects 80% or more of light with wavelengths of 200 nm or less.

The cyclone structure 33 forms a channel for irradiation with the ultraviolet light 12. The cyclone structure 33 is disposed on the surface of the second substrate 3 facing away from the discharge space 10. The cyclone structure 33 includes a tubular structure 14 that swirls a fluid flowing from outside and a tapered structure 13 that directs the fluid swirling in the tubular structure 14 out of the cyclone structure 33.

The thus-constructed ultraviolet irradiation apparatus 30 irradiates a fluid flowing through the cyclone structure 33 with ultraviolet light (e.g. deep-ultraviolet light) 12 containing a reduced amount of light with wavelengths of 200 nm or less. Thus, unlike mercury lamps, the ultraviolet irradiation apparatus 30 can irradiate a fluid with ultraviolet light (e.g. deep-ultraviolet light) that generates a reduced amount of ozone. The ultraviolet irradiation apparatus 30 can also efficiently irradiate a fluid with ultraviolet light since the fluid swirls in the cyclone structure 33. This increases the effective reaction time for organic substances to be decomposed, so that they can be efficiently decomposed.

The deep-ultraviolet light-emitting device 31, the ultraviolet light filter 32, and the cyclone structure 33 will now be described in greater detail.

Deep-Ultraviolet Light-Emitting Device 31

The deep-ultraviolet light-emitting device 31 has a generally prismatic tubular structure (e.g., with a length of 5 to 10 cm, a width of 5 to 10 cm, and a height of 3 to 5 cm). The deep-ultraviolet light-emitting device 31 includes a first substrate 2 and a second substrate 3 that are joined together with a sealant 8 therebetween. On the first substrate 2, electrodes 7 and a dielectric layer 6 are provided. The electrodes apply a voltage for inducing discharge in the discharge space 10. The dielectric layer 6 covers the electrodes 7. On the first substrate 2, a protective layer 5 and a light-emitting layer 4 are also provided. The protective layer 5 protects the dielectric layer 6 from ion bombardment. The light-emitting layer 4 emits deep-ultraviolet light on the surface of the dielectric layer 6 facing the discharge space 10. The protective layer 5 is optional and may be omitted.

The first substrate 2 and the second substrate 3 are hermetically sealed on the periphery thereof, for example, with the sealant 8. The hermetically sealed discharge space 10 is filled with a discharge gas such as xenon (Xe), krypton chloride (KrCl), fluorine ($F_2$), neon (Ne), helium (He), carbon monoxide (CO), or nitrogen ($N_2$) at a predetermined pressure.

A mixture of neon (Ne) and xenon (Xe) is suitable as a discharge gas if magnesium oxide (MgO) powder is used for the light-emitting layer 4, described later. Magnesium oxide (MgO) powder, which has a wide band gap, emits light most efficiently in response to excitation light with a wavelength around 150 nm. If the discharge gas is krypton chloride (KrCl) or xenon (Xe) alone, excitation light containing a large proportion of light with wavelengths above 172 nm is generated in the discharge space 10. If the discharge gas is a mixture of neon (Ne) and xenon (Xe), excitation light containing a large proportion of light with a wavelength of 147 nm is generated in the discharge space 10. It is thus desirable to use a mixture of neon (Ne) and xenon (Xe) as a discharge gas for deep-ultraviolet light-emitting devices in which magnesium oxide (MgO) powder is used for the light-emitting layer 4.

The second substrate 3 is made of a material that transmits deep-ultraviolet light so that the deep-ultraviolet light emitted from the light-emitting layer 4 can be output from the deep-ultraviolet light-emitting device 31 (in this example, upward). Examples of materials that transmit deep-ultraviolet light include special glasses transparent to deep-ultraviolet light, quartz glass ($SiO_2$), magnesium fluoride ($MgF_2$), calcium fluoride ($CaF_2$), lithium fluoride (LiF), and sapphire glass ($Al_2O_3$). Among these materials, sapphire may be used as a material that transmits deep-ultraviolet light since the thermal expansion coefficient thereof is close to those of common glasses and MgO and CaO thin films, which are used for the protective layer 5. The use of sapphire as a material for the second substrate 3 reduces the risk of fracturing and cracking of the protective layer 5 and the sealant 8.

The first substrate 2 may be made of the same material as the second substrate 3 or may be made of a common high-strain-point glass.

For reasons of luminous efficiency and ease of fabrication, a phosphor that emits deep-ultraviolet light is used as a material for the light-emitting layer 4. Examples of phosphors include materials doped with rare-earth luminescence centers, such as $YPO_4$:Pr, $YPO_4$:Nd, $LaPO_4$:Pr, $LaPO_4$:Nd, $YF_3$:Ce, $SrB_6O_{10}$:Ce, YOBr:Pr, $LiSrAlF_6$:Ce, $LiCaAlF_6$:Ce, $LaF_3$:Ce, $Li_6Y(BO_3)_3$:Pr, $BaY_2F_8$:Nd, YOCl:Pr, $YF_3$:Nd, $LiYF_4$:Nd, $BaY_2F_8$:Pr, $K_2YF_5$:Pr, and $LaF_3$:Nd; and materials capable of crystal defect emission or band gap emission, such as MgO, ZnO, AlN, diamond, and BN.

In particular, magnesium oxide (MgO) powder is suitable as a material for the light-emitting layer 4. As disclosed in Japanese Unexamined Patent Application Publication No. 2010-80440, magnesium oxide (MgO) powder has an emission intensity peak in the wavelength range from 200 to 300 nm. Specifically, magnesium oxide (MgO) powder emits deep-ultraviolet light with a peak around 230 nm. In addition, since magnesium oxide (MgO) has superior secondary electron emission characteristics, a phosphor material doped with a rare-earth luminescence center can be used for the light-emitting layer 4 to achieve low discharge onset voltage. Magnesium oxide (MgO) also has high ion bombardment resistance, which results in less damage to the light-emitting layer 4 due to ion bombardment. It is thus effective to use magnesium oxide (MgO) powder for the light-emitting layer 4 in the deep-ultraviolet light-emitting device 31.

If the light-emitting layer 4 is a film of powder, film adhesion should be considered. Accordingly, irregularities may be formed on the surface on which the light-emitting layer 4 is to be formed to maintain the shape of the film of powder that forms the light-emitting layer 4. This improves the adhesion of the light-emitting layer 4 to the substrate (first substrate 2 and second substrate 3).

The light-emitting layer 4 is formed on the dielectric layer 6 covering the electrodes 7 or on the protective layer 5 formed on the dielectric layer 6. To enhance the discharge intensity, the light-emitting layer 4 may be formed not only on the first substrate 2, but also on the surface of the second substrate 3 facing the discharge space 10 and the surface of the second substrate 3 facing away from the discharge space 10 (i.e., between the second substrate 3 and the ultraviolet light filter 32).

The protective layer 5 may be disposed below the light-emitting layer 4. For example, the protective layer 5 may be a thin layer of magnesium oxide (MgO), calcium oxide (CaO), barium oxide (BaO), strontium oxide (SrO), or a mixture thereof. The use of a thin layer of magnesium oxide (MgO), which has high ion bombardment resistance, as the protective layer 5 provides a deep-ultraviolet light-emitting device that exhibits only a minimal decrease in discharge intensity over time.

The dielectric layer 6 is formed by a process such as screen printing and has a thickness of about 30 μm. The dielectric layer 6 is made of a low-melting-point glass containing a major proportion of lead oxide (PbO), bismuth oxide ($Bi_2O_3$), or phosphorus oxide ($PO_4$). As used herein, the term "major proportion" refers to 50% by weight or more of the total composition of the dielectric layer 6. Since the dielectric layer 6, which is made of an insulating material, covers the electrodes 7, the form of discharge is dielectric barrier discharge. Dielectric barrier discharge, in which the electrodes 7 are not directly exposed to ions, causes only a small change in luminous intensity over time during continuous operation and is therefore suitable for applications requiring extended operating time, such as sterilization and lithography. The thickness of the dielectric layer 6, which affects the field intensity in the discharge space 10, may be changed depending on the size of the deep-ultraviolet light-emitting device 31 and the desired properties.

The dielectric layer 6 may be formed only on the electrodes 7. This reduces the amount of deep-ultraviolet light absorbed by the dielectric layer 6 and thus allows the deep-ultraviolet light emitted from the light-emitting layer 4 to be efficiently output from the deep-ultraviolet light-emitting device 31. For example, the dielectric layer 6 may be formed only on the electrodes 7 by applying a paste containing a major proportion of a low-melting-point glass to the electrodes 7 using a screen mask through which the paste can be applied only to the electrode regions, followed by firing.

The electrodes 7 are organized into pairs of two parallel strip-shaped (or elongated) electrodes arranged on the main surface of the first substrate 2. The electrodes 7 may be made of, for example, a thick Ag film, a thin Al film, or a thin Cr/Cu/Cr multilayer film. Alternating voltages of various waveforms, such as rectangular and sinusoidal waveforms, are applied to the pairs of electrodes 7. Typically, voltages of opposite phase are applied to the electrodes 7 of each pair, which results in intense light emission. Discharge can also be induced by applying a rectangular voltage to one of the electrodes 7 of each pair while grounding the other electrode 7. The electrodes 7 are not necessarily organized into pairs, but may be organized into groups of more than two electrodes 7, depending on the position and shape of the discharge space 10 or to reduce the discharge onset voltage.

The sealant 8 may be a $Bi_2O_3$— or $V_2O_5$-based frit. An example $Bi_2O_3$-based frit is a $Bi_2O_3$—$B_2O_3$—RO-MO-based (where R is Ba, Sr, Ca, or Mg, and M is Cu, Sb, or Fe) glass material containing an oxide filler such as $Al_2O_3$, $SiO_2$, or cordierite. An example $V_2O_5$-based frit is a $V_2O_5$—BaO—TeO—WO-based glass material containing an oxide filler such as $Al_2O_3$, $SiO_2$, or cordierite.

An exhaust tube 9 is joined to the first substrate 2 or to the second substrate 3 (in this example, only to the first substrate 2) with the sealant 8. The substrate to which the exhaust tube 9 is joined (in this example, the first substrate 2) has a through-hole 11 through which the discharge space 10 can be filled with a discharge gas. The exhaust tube 9 is used to evacuate the discharge space 10 and to fill the discharge space 10 with the discharge gas and is sealed off by heating the end thereof so that no discharge gas leaks from the discharge space 10 after filling with the discharge gas. Exhaust tubes 9 may be provided for evacuation and filling with the discharge gas.

When a voltage is applied to the electrodes 7 in the thus-constructed deep-ultraviolet light-emitting device 31, the light-emitting layer 4 emits ultraviolet light (particularly, deep-ultraviolet light) 12 upward (i.e., toward the ultraviolet light filter 32). Specifically, sinusoidal or rectangular voltages of opposite phase are applied to the adjacent electrodes 7 of each pair to generate an intense electric field between the two electrodes 7. This electric field causes discharge in the discharge gas sealed in the discharge space 10. The xenon (Xe) and krypton chloride (KrCl) present in the discharge gas are excited by discharge to emit excitation light such as vacuum ultraviolet light or deep-ultraviolet light. The light-emitting layer 4 is then irradiated with the excitation light to emit ultraviolet light (particularly, deep-ultraviolet light) 12. The ultraviolet light 12 emitted from the light-emitting layer 4 passes through the second substrate 3.

Ultraviolet Light Filter 32

The ultraviolet light filter 32 is disposed on the deep-ultraviolet light-emitting device 31 and absorbs or reflects 80% or more of light with wavelengths of 200 nm or less. In this embodiment, the ultraviolet light filter 32 has substantially the same contour as the deep-ultraviolet light-emitting device 31 (or the second substrate 3) in plan view (i.e., as viewed from top to bottom in the drawings). The ultraviolet light filter 32 is joined to the deep-ultraviolet light-emitting device 31 with a material (sealing material)

such as the sealant 8 such that the ultraviolet light filter 32 covers the deep-ultraviolet light-emitting device 31 (i.e., the second substrate 3).

The use of an ultraviolet light filter 32 made of a titanium-containing glass attenuates ultraviolet light with extremely short wavelengths of 200 nm or less, thus reducing the generation of ozone.

Cyclone Structure 33

The cyclone structure 33 forms a channel for irradiation with the ultraviolet light 12 emitted from the deep-ultraviolet light-emitting device 31 and passing through the ultraviolet light filter 32. The cyclone structure 33 is disposed on the ultraviolet light filter 32 and is made of, for example, a metal (e.g., stainless steel or aluminum). The cyclone structure 33 includes a tubular structure 14 that swirls a fluid flowing from outside and a tapered structure 13 that directs the fluid swirling in the tubular structure 14 out of the cyclone structure 33.

FIGS. 2A and 2B illustrate the construction of the cyclone structure 33 shown in FIG. 1. FIG. 2A is a top view (plan view) of the cyclone structure 33. FIG. 2B is a sectional view of the cyclone structure 33 taken in a plane including line IIB-IIB in FIG. 1 (i.e., in a plane perpendicular to the page).

The tubular structure 14 has substantially the same contour as the deep-ultraviolet light-emitting device 31 and the ultraviolet light filter 32 in plan view. The tubular structure 14 is joined to the ultraviolet light filter 32 with a material (sealing material) such as the sealant 8 such that the tubular structure 14 covers the ultraviolet light filter 32. In this embodiment, the tubular structure 14 is a prismatic tubular structure having an open top and an open bottom. The tubular structure 14 has an inlet 15 for introducing a fluid into the tubular structure 14 and curved inner walls 17 for preventing the retention of the fluid due to eddy currents at the four corners. As shown in FIGS. 1, 2A, and 2B, the inlet 15 is formed by a pipe extending through a side surface of the tubular structure 14. The inner walls 17 are formed by curved plates covering the four corners of the inner walls.

The tapered structure 13 has substantially the same contour as the deep-ultraviolet light-emitting device 31 and the ultraviolet light filter 32 in plan view. The tapered structure 13 is joined to the tubular structure 14 by a technique such as welding such that the tapered structure 13 covers the tubular structure 14. In this embodiment, the tapered structure 13 is a quadrangular pyramid structure having an open bottom. The tapered structure 13 has an outlet 16 for releasing the fluid from the tapered structure 13 at the apex thereof.

The thus-constructed cyclone structure 33 forms a channel through which a fluid such as air or water passes for sterilization and decomposition cleaning above the deep-ultraviolet light-emitting device 31 (i.e., above the ultraviolet light filter 32). This channel increases the time for the fluid to reside in the cyclone structure 33 and thus increases the effective ultraviolet irradiation time, so that sterilization and decomposition cleaning can be efficiently performed with less ultraviolet light. Since this channel has a cyclone structure, the time for the fluid to reside in the cyclone structure 33 is at least one order of magnitude longer than without such a channel.

The tubular structure 14 has an aspect ratio ha/hc of 5 to 30, desirably 6 to 20, more desirably 7 to 10, where ha is the diameter of a circle inscribed in the bottom surface of the tubular structure 14, and hc is the height of the tubular structure 14. The tubular structure 14 has a height hc of 2 to 30 mm, desirably 4 to 20 mm, more desirably 5 to 10 mm. If the tubular structure 14 has a height hc of 2 mm or more, the fluid flows at a sufficient flow rate, which results in improved processing efficiency. If the tubular structure 14 has a height hc of 30 mm or less, the fluid can be sterilized with deep-ultraviolet light with sufficiently reduced attenuation in the top of the tubular structure 14. If the tubular structure 14 has an aspect ratio ha/hc of 5 or more, the distance between the deep-ultraviolet light-emitting device 31 and the fluid is so small that the fluid can be sterilized with deep-ultraviolet light with reduced attenuation near the apex of the tapered structure 13. If the tubular structure 14 has an aspect ratio ha/hc of 30 or less, a swirling flow unique to cyclone structures occurs. This allows the fluid to be uniformly irradiated with the ultraviolet radiation emitted from the deep-ultraviolet light-emitting device 31, which is a surface-emitting device, so that the fluid can be efficiently sterilized.

A method for manufacturing the thus-constructed ultraviolet irradiation apparatus 30 according to this embodiment will now be described.

The electrodes 7 are first formed on the first substrate 2. The electrodes 7 may be formed by known patterning processes such as exposure, printing, and evaporation.

A dielectric paste (dielectric material) layer is then formed over the electrodes 7 formed on the first substrate 2. A dielectric paste is applied to the first substrate 2 by a process such as die coating and is left standing for a predetermined period of time to level the dielectric paste layer into a smooth surface. The dielectric paste layer is then solidified by firing to form the dielectric layer 6 over the electrodes 7. The dielectric paste contains, for example, a dielectric material such as glass powder, a binder, and a solvent.

The light-emitting layer 4 is then the formed on the dielectric layer 6. The light-emitting layer 4 may be formed by applying a paste containing a light-emitting material to the desired region and then drying and firing the paste.

The light-emitting layer 4 is also formed on the second substrate 3. The light-emitting layer 4 formed on the second substrate 3 is thinner than that formed on the first substrate 2 and may be formed in the same manner as that formed on the first substrate 2.

Optionally, the protective layer 5 is formed between the dielectric layer 6 and the light-emitting layer 4. The protective layer 5 functions to lower the voltage at which discharge occurs (discharge onset voltage) and to protect the dielectric layer 6 and the electrodes 7 from ion bombardment due to discharge. The protective layer 5 is typically formed by thin-film deposition processes using pellets of materials such as magnesium oxide (MgO), calcium oxide (CaO), strontium oxide (SrO), barium oxide (BaO), and mixtures thereof. Examples of thin-film deposition processes include known processes such as electron beam evaporation, sputtering, and ion plating. For example, the practical upper pressure limit is 1 Pa for sputtering and is 0.1 Pa for electron beam evaporation, which is a type of evaporation.

The sealant 8 is then applied to at least one of the first substrate 2 and the second substrate 3 and is calcined at about 350° C. to remove volatile components such as resin from the sealing material.

The thus-prepared first substrate 2 and second substrate 3 are then sealed by bonding.

A sealing/evacuation oven used in the sealing step will now be described. FIG. 3 is a schematic view illustrating the construction of a sealing/evacuation oven 100 for the manufacture of the deep-ultraviolet light-emitting device 31 according to the first embodiment.

The sealing/evacuation oven 100 includes an oven unit 52 having a heater 51 built thereinto. In the oven unit 52 in FIG. 3, the first substrate 2 having the calcined sealant 8 and the exhaust tube 9 (in this example, exhaust tubes 9a and 9b) is stacked on the second substrate 3.

The first substrate 2 is secured to the second substrate 3 and to the exhaust tubes 9a and 9b with fasteners (not shown) such as clips.

The exhaust tube 9a is connected to a pipe 53. The pipe 53 is in turn connected via a valve 61 to a dry gas supply unit 71 disposed outside the oven unit 52. The pipe 53 is provided with a gas release valve 62.

The exhaust tube 9b is connected to a pipe 54. The pipe 54 is in turn connected via a valve 63 to an evacuation unit 72 disposed outside the oven unit 52. The pipe 54 is also connected via a valve 64 to a discharge gas supply unit 73 disposed outside the oven unit 52. The pipe 54 is also connected via a valve 65 to the pipe 53. The pipe 54 is provided with a pressure gauge 66.

Figure 4:
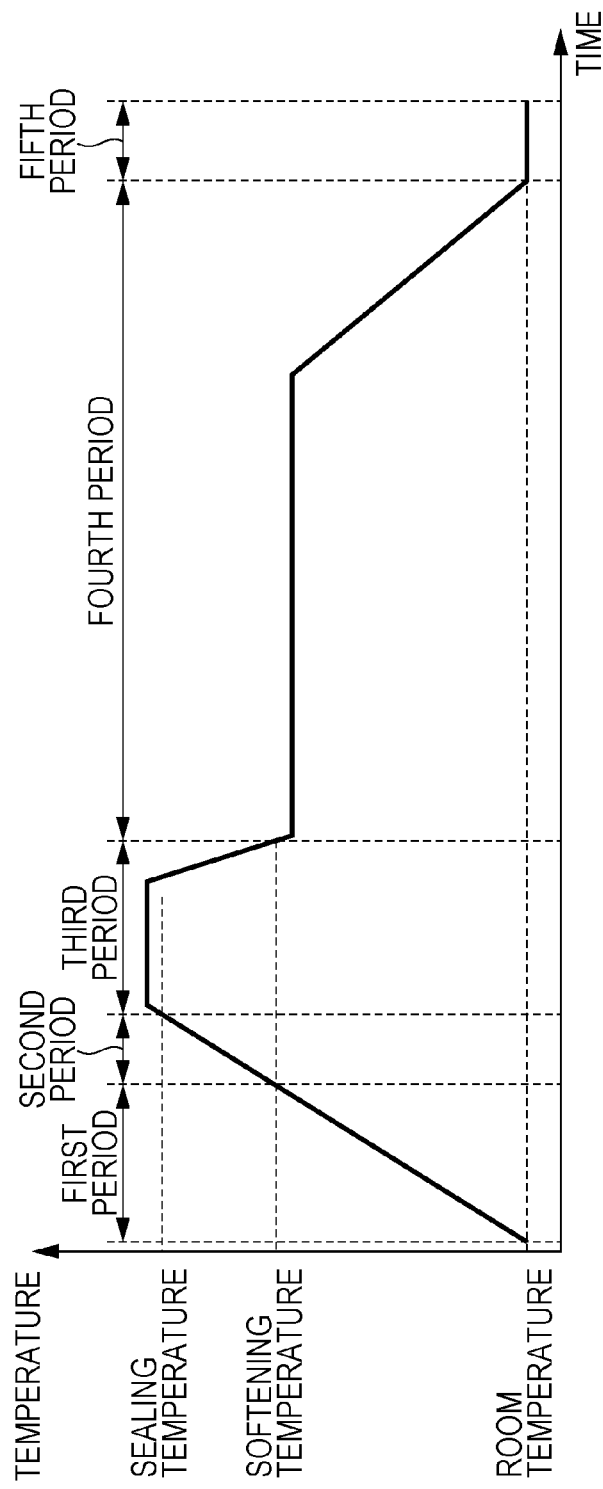
FIG. 4 is a graph showing an example temperature profile of the sealing/evacuation oven shown in FIG. 3.

FIG. 4 is a graph showing an example temperature profile of the sealing/evacuation oven 100 shown in FIG. 3.

The profile of the sealing step and the subsequent evacuation and discharge gas supply steps will now be described in detail in order. For illustration purposes, the sealing step and the subsequent evacuation and discharge gas supply steps are divided into the following five periods according to temperature.

The five periods are a period in which the temperature is increased from room temperature to the softening temperature (first period), a period in which the temperature is increased from the softening temperature to the sealing temperature (second period), a period in which the temperature is maintained at or above the sealing temperature for a predetermined period of time and is then decreased to the softening temperature (third period), a period in which the temperature is maintained near or slightly below the softening temperature for a predetermined period of time and is then decreased to room temperature (fourth period, corresponding to the evacuation step), and a period after the temperature is decreased to room temperature (fifth step, corresponding to the discharge gas supply step). The first to third periods correspond to the sealing step.

The term "softening temperature" refers to the temperature at which the sealant 8 softens. For example, bismuth oxide ($Bi_2O_3$)-based sealing materials have softening temperatures of about 430° C.

The term "sealing temperature" refers to the temperature at which the first substrate 2 and the second substrate 3 are sealed by the sealant 8 or the temperature at which the first substrate 2 and the exhaust tubes 9 are sealed by the sealing material (not shown). In this embodiment, the sealing temperature is, for example, about 490° C. The sealing temperature may be determined in advance as follows.

Specifically, the first substrate 2 and the second substrate 3 are stacked on top of each other. The valves 61, 64, and 65 are closed, and only the valve 63 is opened. While the discharge space 10 is evacuated through the exhaust tube 9b with the evacuation unit 72, the heater 51 is turned on to increase the inner temperature of the oven unit 52. When a certain temperature is reached, the pressure of the discharge space 10 read on the pressure gauge 66 decreases stepwise and does not increase considerably even after the valve 63 is closed. This temperature is the sealing temperature at which the discharge space 10 is sealed.

The sealing step will now be described in detail with reference to FIGS. 5A to 5E. FIGS. 5A to 5E illustrate the flow of gases through the discharge space 10 during the first to fifth periods, respectively.

Figure 5:
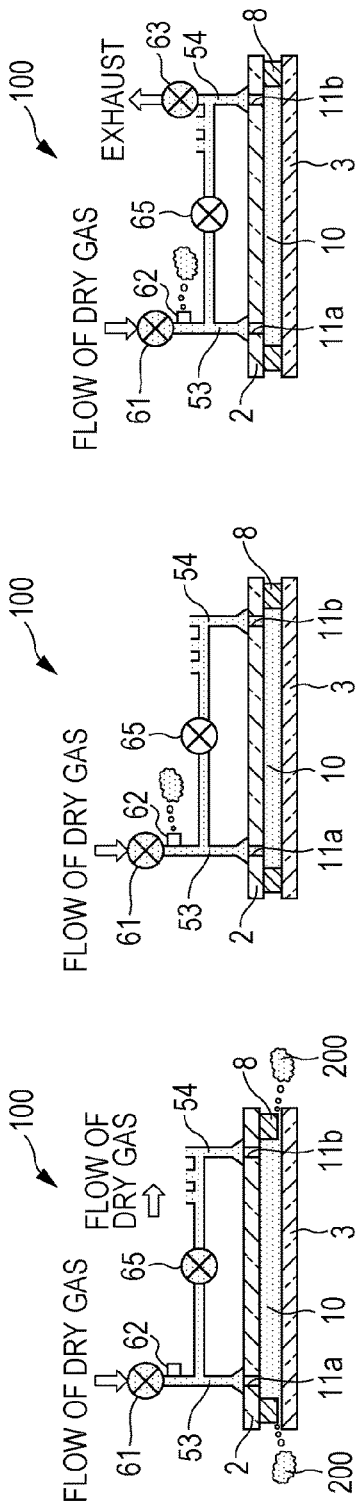
FIGS. 5A to 5E illustrate the flow of gases through the discharge space during a sealing step in the sealing/evacuation oven shown in FIG. 3.

The first substrate 2 and the second substrate 3 are first positioned and stacked on top of each other. As shown in FIG. 5A, the valves 61 and 65 are opened, and a dry gas is supplied through two through-holes 11 (11a and 11b) to the discharge space 10. While the dry gas is supplied, the heater 51 is turned on to increase the inner temperature of the oven unit 52 to the softening temperature of the sealant 8.

As indicated by reference numeral 200 in FIG. 5A, the dry gas supplied to the discharge space 10 leaks from the discharge space 10 through a gap between the first substrate 2 or second substrate 3 and the sealant 8 disposed thereon.

The dry gas may be dry nitrogen gas with a dew point of −45° C. or lower. The flow rate is typically 5 L/min (first period).

As shown in FIG. 5B, when the inner temperature of the oven unit 52 increases to the softening temperature of the sealing frit or higher, the valve 65 is closed, and the valve 61 is adjusted to control the flow rate of the dry gas to less than half the flow rate during the first period, for example, to 2 L/min. The gas release valve 62 is then opened to control the pressure of the discharge space 10 to a slightly positive pressure relative to the inner pressure of the oven unit 52. The inner temperature of the oven unit 52 is then increased to the sealing temperature (second period).

When the inner temperature of the oven unit 52 increases to the sealing temperature or higher, the sealant 8 melts, thereby sealing the first substrate 2 and the second substrate 3 and bonding the exhaust tubes 9a and 9b to the first substrate 2. As shown in FIG. 5C, the evacuation unit 72 is started, and the valve 63 is adjusted to control the pressure of the discharge space 10 to a slightly negative pressure, for example, $8.0 \times 10^4$ Pa. In this way, the dry gas is supplied through the exhaust tube 9a and is exhausted through the exhaust tube 9b to maintain the pressure of the discharge space 10 at a slightly negative pressure while continuing the supply of dry nitrogen gas to the discharge space 10.

The heater 51 is controlled to maintain the inner temperature of the oven unit 52 at or above the sealing temperature for about 30 minutes. During this process, the molten sealant flows slightly, and the pressure of the discharge space 10 is maintained at a slightly negative pressure. This allows the first substrate 2 and the second substrate 3 to be accurately sealed and the exhaust tubes 9a and 9b to be accurately bonded to the first substrate 2. The heater 51 is then turned off to decrease the temperature of the oven unit 52 to the softening temperature or lower (third period).

Evacuation Step

In the evacuation step, the discharge space 10 is evacuated. As shown in FIG. 5D, when the inner temperature of the oven unit 52 decreases to the softening temperature or lower, the valve 61 is closed, and the valves 63 and 65 are opened to evacuate the discharge space 10 through the through-holes 11 (11a and 11b) and the exhaust tubes 9a and 9b. The heater 51 is then controlled to maintain the inner temperature of the oven unit 52 for a predetermined period of time while continuing evacuation. The heater 51 is then turned off to decrease the temperature of the oven unit 52 to room temperature. During this process, evacuation is continued (fourth period).

Discharge Gas Supply Step

In the discharge gas supply step, a discharge gas containing a major proportion of gases such as neon (Ne) and xenon (Xe) is supplied to the evacuated discharge space 10. As shown in FIG. 5E, when the inner temperature of the oven unit 52 decreases to room temperature, the valve 63 is closed, and the valves 64 and 65 are opened to supply the discharge gas to a predetermined pressure through the exhaust tubes 9a and 9b and the through-holes 11 (11a and 11b). The exhaust tubes 9a and 9b are then sealed off by heating the ends thereof (i.e., the ends connected to the pipes 53 and 54, respectively).

In this way, the first substrate 2 and the second substrate 3 having the predetermined components are secured and sealed on the periphery thereof with the sealant 8, and the discharge space 10 is filled with a discharge gas containing gases such as xenon (Xe) and neon (Ne). The deep-ultraviolet light-emitting device 31 is finished.

Finally, the ultraviolet light filter 32 is joined to the finished deep-ultraviolet light-emitting device 31 with a material (sealing material) such as the sealant 8, and the cyclone structure 33 is joined to the ultraviolet light filter 32 with a material (sealing material) such as the sealant 8.

After these steps, the ultraviolet irradiation apparatus 30 is finished.

Examples

Examples will now be described. In the examples, ultraviolet irradiation apparatuses according to the first embodiment and ultraviolet irradiation apparatuses of comparative examples were fabricated and tested for their characteristics. The ultraviolet irradiation apparatuses were fabricated as described above.

The construction of the ultraviolet irradiation apparatuses is as shown in FIG. 1. The second substrate 3 was made of sapphire glass, which transmits deep-ultraviolet light. The light-emitting layer 4 was formed on the surface of the second substrate 3 facing the discharge space 10. The sapphire glass was polished only on one surface thereof. The surface of the second substrate 3 facing the discharge space 10 was left unpolished so that the light-emitting layer 4 had improved adhesion to the second substrate 3.

A titanium-containing glass was placed as the ultraviolet light filter 32 on the sapphire glass forming the second substrate 3, and the cyclone structure 33 was placed thereon to form a channel.

The discharge space 10 of the deep-ultraviolet light-emitting device 31 was filled with a discharge gas containing 95% Ne and 5% Xe to a pressure of 10 kPa.

The protective layer 5 was deposited to a thickness of 1 μm on the dielectric layer 6 by electron beam vacuum evaporation of magnesium oxide (MgO).

A rectangular voltage with a frequency of 30 kHz was applied to the electrodes 7. Specifically, rectangular voltages of opposite phase were applied to the electrodes 7 of each pair. The discharge onset voltage was determined as follows. The rectangular voltage applied to the electrodes 7 was first increased to 950 V to induce light emission from the deep-ultraviolet light-emitting device 31. The voltage was then decreased to 0 V to terminate light emission over the entire deep-ultraviolet light-emitting device 31. The voltage was increased again, and the voltage at which the discharge spread over the entire discharge space 10 was measured to determine the discharge onset voltage.

Figure 6:
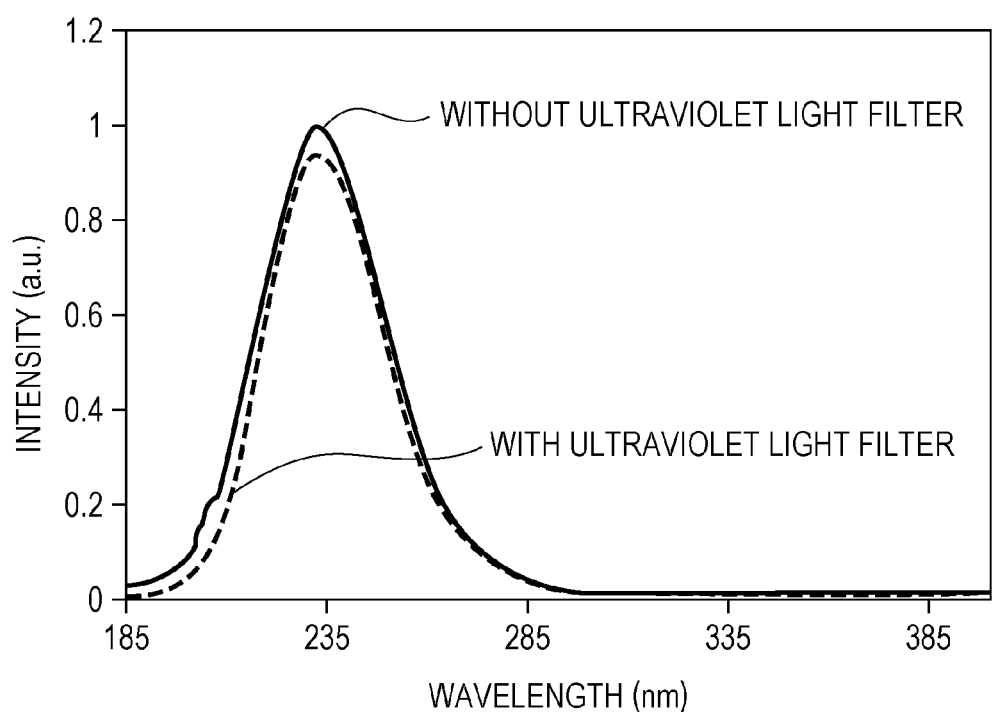
FIG. 6 is a graph comparing emission spectra obtained from ultraviolet irradiation apparatuses with and without an ultraviolet light filter.

Emission spectra were obtained with a multichannel spectrometer (C10027-01, Hamamatsu Photonics K.K.) on the outermost surface of the second substrate 3 before the cyclone structure 33 was placed thereon. Emission spectra were obtained with and without the ultraviolet light filter 32 and were compared. FIG. 6 is a graph comparing the emission spectra obtained with and without the ultraviolet light filter 32. The emission of deep-ultraviolet light from magnesium oxide (MgO) was observed around 230 nm. The graph shows that the presence of the ultraviolet light filter 32 resulted in decreased luminous intensity around 200 nm.

To measure and compare the ability of the ultraviolet irradiation apparatuses to decompose organic substances, a deodorization test was conducted by supplying odorant-containing air (gas to be treated) to the channel or cyclone structure 33 at a flow rate of 12 L/min. The odorants were 10 ppm hydrogen sulfide, 0.5 ppm methyl mercaptan, and 2 ppm ammonia. The ozone concentration was 30 ppm without a filter under blank conditions where no odorant was supplied.

Table 1 shows the construction of the four ultraviolet irradiation apparatuses fabricated in the examples (Comparative Examples 1 and 2 and Examples 1 and 2).

TABLE 1

| | Ultraviolet light filter | Cyclone structure | Curved wall |
|---|---|---|---|
| Comparative Example 1 | None | None | None |
| Comparative Example 2 | Provided | None | None |
| Example 1 | Provided | Provided | None |
| Example 2 | Provided | Provided | Provided |

Table 2 shows the reduction in odorant content and the ozone concentration at the outlets of the ultraviolet irradiation apparatuses fabricated in the examples.

TABLE 2

| | Hydrogen sulfide | Methyl mercaptan | Ammonia | Ozone |
|---|---|---|---|---|
| Comparative Example 1 | 76% | 78% | 45% | 22 ppm |
| Comparative Example 2 | 7% | 8% | 4% | 3 ppm |
| Example 1 | 91% | 94% | 60% | 1 ppm |
| Example 2 | 96% | 98% | 64% | 0 ppm |

As can be seen from Table 2, the ozone concentration at the outlet of the ultraviolet irradiation apparatus of Comparative Example 2, in which an ultraviolet light filter was provided, was one order of magnitude smaller than that of Comparative Example 1, in which no ultraviolet light filter was provided, and accordingly, the reduction in odorant content of Comparative Example 2 was about one order of magnitude smaller than that of Comparative Example 1. The ozone concentration at the outlet of the ultraviolet irradiation apparatus of Example 1 was one twentieth that of Comparative Example 1; however, the reduction in odorant content of Example 1 was about 20% higher than that of Comparative Example 1, indicating that the decomposition reaction was facilitated. In Example 2, in which curved plates were provided at the four corners of the inner walls of the tubular structure, nearly all hydrogen sulfide and methyl mercaptan were decomposed, and more than 60% of ammonia was also decomposed, even though there was no ozone at the outlet. The significant reduction in odorant content of Example 2 is attributable to the fact that the curved plates reduced the flow resistance of the inner walls of the cyclone structure and increased the rotational moment of the swirling flow, thereby increasing the time for the fluid to reside in the cyclone structure and promoting the reaction.

These results demonstrate that the use of the construction of Example 1 or 2 in this embodiment provides an ultraviolet irradiation apparatus that can effectively decompose odorants while generating less ozone, which is harmful to humans.

Although the second substrate 3 and the ultraviolet light filter 32 of the ultraviolet irradiation apparatus 30 according to the first embodiment are separate components stacked on top of each other, they may be formed as a unitary component.

Figure 7:
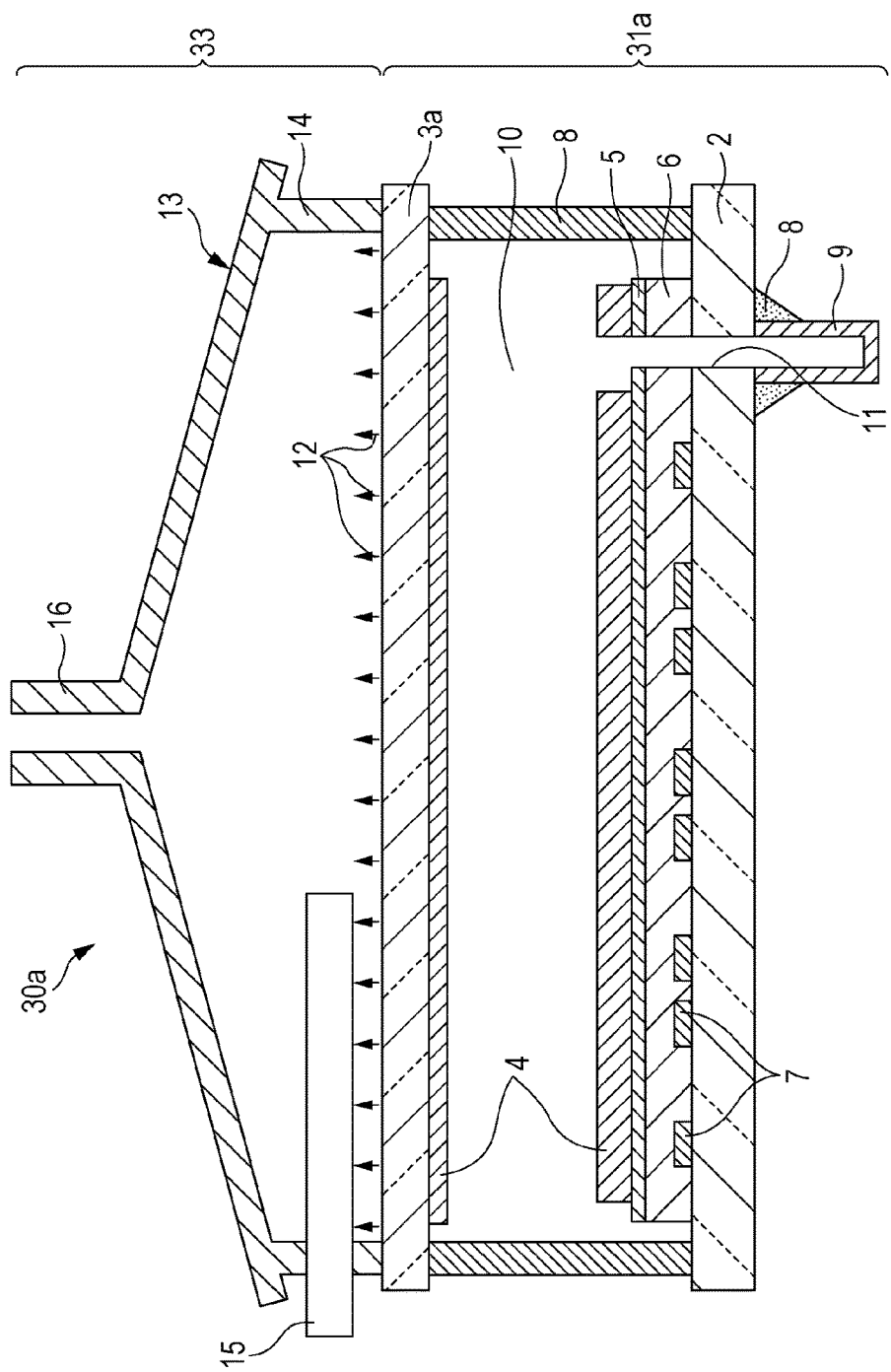
FIG. 7 is a schematic sectional view illustrating the construction of an ultraviolet irradiation apparatus according to a modification of the first embodiment.

FIG. 7 is a schematic sectional view illustrating the construction of an ultraviolet irradiation apparatus 30a according to a modification of the first embodiment in which a second substrate and an ultraviolet light filter are formed as a unitary component. The ultraviolet irradiation apparatus 30a differs from the ultraviolet irradiation apparatus 30 according to the first embodiment in that the second substrate 3 and the ultraviolet light filter 32 in the first embodiment are replaced with a second substrate 3a that functions as an ultraviolet light filter. That is, a deep-ultraviolet light-emitting device 31a according to this modification includes the second substrate 3a. The other elements are identical to those of the ultraviolet irradiation apparatus 30 according to the first embodiment. The second substrate 3a in this modification functions both as the second substrate 3 and as the ultraviolet light filter 32 in the first embodiment. Specifically, the second substrate 3a transmits deep-ultraviolet light while absorbing or reflecting 80% or more of light with wavelengths of 200 nm or less. For example, the second substrate 3a is made of a special glass transparent to ultraviolet light, quartz glass ($SiO_2$), magnesium fluoride ($MgF_2$), calcium fluoride ($CaF_2$), lithium fluoride (LiF), or sapphire glass ($Al_2O_3$) and contains titanium.

The ultraviolet irradiation apparatus 30a according to this modification, in which the second substrate and the ultraviolet light filter are formed as a unitary component, provides the same advantages as and has a simpler structure than the ultraviolet irradiation apparatus 30 according to the first embodiment.

Second Embodiment

Figure 9:
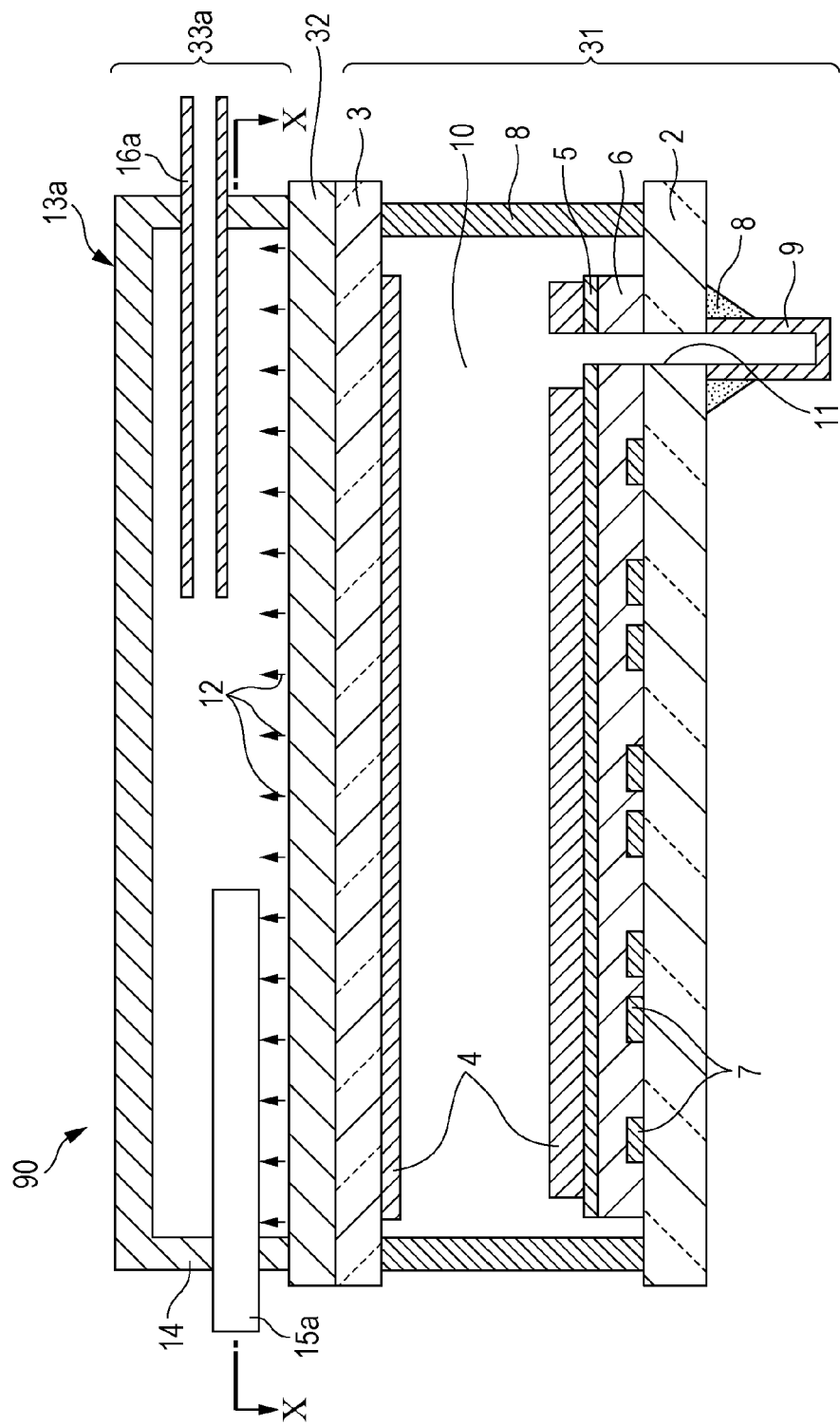
FIG. 9 is a schematic sectional view illustrating the construction of an ultraviolet irradiation apparatus according to a second embodiment.

FIG. 9 is a schematic sectional view illustrating the construction of an ultraviolet irradiation apparatus 90 according to a second embodiment. In the first embodiment and the modification thereof, the cyclone structure 33 is used as a reaction vessel for irradiating a fluid flowing from outside with ultraviolet radiation; the ultraviolet irradiation apparatus 90 according to the second embodiment differs from the ultraviolet irradiation apparatus 30 according to the first embodiment in that the cyclone structure 33 is replaced with a reaction vessel 33a. The other elements of the ultraviolet irradiation apparatus 90 according to the second embodiment are identical to those of the first embodiment. In this embodiment, the same or similar elements as those of the first embodiment are indicated by the same reference numerals to avoid duplication of description.

Figure 10:
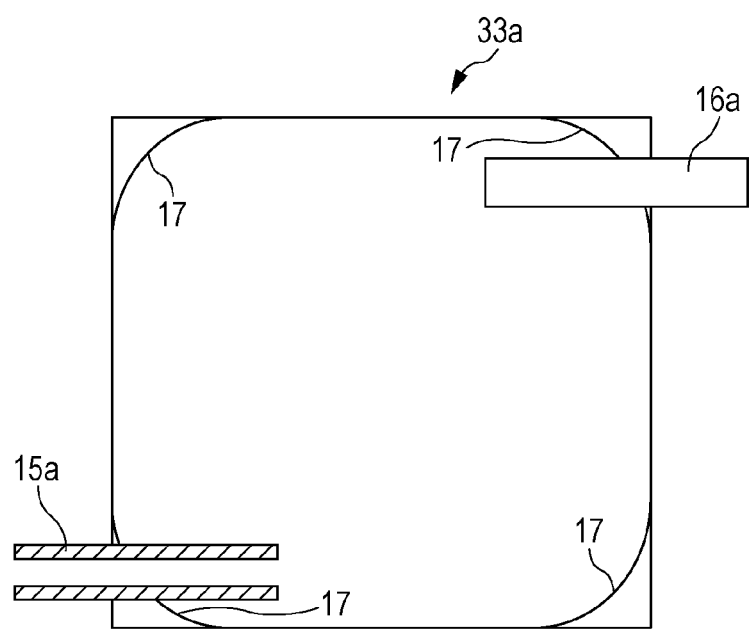
FIG. 10 illustrates a reaction vessel shown in FIG. 9.

To irradiate a fluid flowing from outside with ultraviolet radiation, the reaction vessel 33a includes a tubular structure 14, an inlet channel 15a, an outlet channel 16a, and a lid 13a. The top of the tubular structure 14 is closed by the lid 13a. The lid 13a and the tubular structure 14 may be formed as a unitary component. The bottom of the tubular structure 14 is closed by the ultraviolet light filter 32. The inlet channel 15a and the outlet channel 16a are formed by pipes extending through side surfaces of the tubular structure 14. The inlet channel 15a directs a fluid flowing from outside the reaction vessel 33a into the tubular structure 14. The outlet channel 16a directs the fluid flowing from inside the tubular structure 14 out of the reaction vessel 33a. The thus-constructed reaction vessel 33a allows a fluid flowing from outside to reside in the tubular structure 14 for a sufficient period of time. The fluid residing in the tubular structure 14 is irradiated with ultraviolet radiation through the ultraviolet light filter 32. To irradiate the fluid with ultraviolet radiation for a longer period of time, the inlet channel 15a and the outlet channel 16a may be arranged at two opposite corners of the tubular structure 14 (see FIGS. 9 and 10).

Third Embodiment

Figure 11:
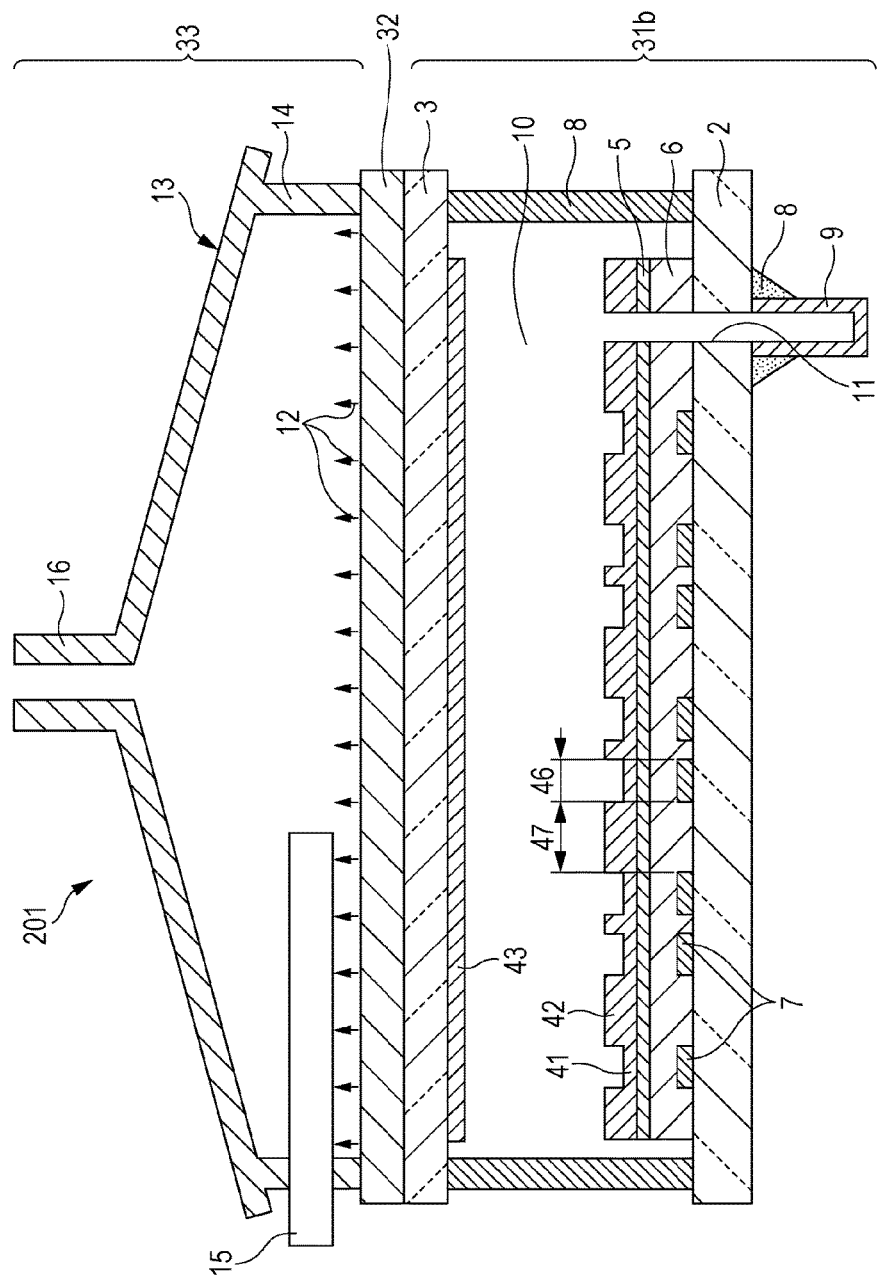
FIG. 11 is a schematic sectional view illustrating the construction of an ultraviolet irradiation apparatus according to a third embodiment.

The construction of an ultraviolet irradiation apparatus 201 according to a third embodiment of the present disclosure will now be described with reference to FIG. 11. FIG. 11 is a sectional view illustrating the construction of the ultraviolet irradiation apparatus 201 according to this embodiment. In this embodiment, the same or similar elements as those of the first embodiment are indicated by the same reference numerals to avoid duplication of description.

The ultraviolet irradiation apparatus 201 according to this embodiment differs from the ultraviolet light-emitting device 30 according to the first embodiment in that first light-emitting layers 41 disposed in regions 46 including at least parts of the regions directly above the electrodes 7 are thinner than second light-emitting layers 42 disposed in regions 47 different from the regions 46. For example, the first light-emitting layers 41 have a thickness of less than 10 μm, and the second light-emitting layers 42 have a thickness of about 20 to 30 μm. A third light-emitting layer 43 may be disposed on the second substrate 3.

The features and advantages of the ultraviolet irradiation apparatus 201 according to this embodiment will now be described. One problem with ultraviolet light-emitting devices including a light-emitting layer directly above electrodes is that the luminous intensity decreases over time during continuous operation. The inventors have discovered that this problem results from two factors: a decrease in the luminous intensity of the light-emitting layer directly above the electrodes due to ion bombardment during discharge, and a decrease in discharge intensity due to changes in the secondary electron emission characteristics of the light-emitting layer directly above the electrodes.

As a solution to this problem, the ultraviolet irradiation apparatus 201 according to this embodiment includes an ultraviolet light-emitting device 31b. The ultraviolet light-emitting device 31b includes a first substrate 2 having a first main surface and a second main surface opposite the first main surface, a second substrate 3 disposed opposite the first main surface of the first substrate 2, electrodes 7 disposed on the first main surface of the first substrate 2, a dielectric layer 6 disposed on the first main surface of the first substrate 2 and covering the electrodes 7, a protective layer 5 disposed on the dielectric layer 6 to protect the dielectric layer 6, and first, second, and third light-emitting layers 41, 42, and 43 that emit ultraviolet light. The first light-emitting layers 41 are disposed on the protective layer 5 in regions 46 including at least parts of the regions directly above the electrodes 7. The second light-emitting layers 42 are disposed on the protective layer 5 in regions 47 different from the regions 46. The first light-emitting layers 41 are thinner than the second light-emitting layers 42; therefore, they form ridges and grooves on the side facing the discharge space 10. The third light-emitting layer 43 is disposed on the surface of the second substrate 3 facing the first substrate 2. The discharge space 10 between the first substrate 2 and the second substrate 3 is filled with a predetermined gas. The first, second, and third light-emitting layers 41, 42, and 43 emit ultraviolet light in response to discharge in the gas between the electrodes 7.

The presence of the thin first light-emitting layers 41 in the regions directly above the electrodes 7 reduces the proportion of the luminous intensity in the regions directly above the electrodes 7 to the total luminous intensity of the ultraviolet light-emitting device 31$b$. Thus, the decrease in the luminous intensity of the first light-emitting layers 41 in the regions directly above the electrodes 7 over time has less effect on the total luminous intensity of the ultraviolet light-emitting device 31$b$. This results in a smaller decrease in the luminous intensity of the ultraviolet light-emitting device 31$b$ over time.

The presence of the thin first light-emitting layers 41 in the regions directly above the electrodes 7 also reduces the coverage of the dielectric layer 6 or the protective layer 5 with the light-emitting layers 41 and 42. Thus, the discharge onset voltage is more affected by the secondary electron emission characteristics of the dielectric layer 6 or the protective layer 5 below the first light-emitting layers 41. The dielectric layer 6 and the protective layer 5 exhibit a smaller change in secondary electron emission characteristics over time than the first light-emitting layers 41. This results in a smaller change in secondary electron emission characteristics during continuous operation and thus a smaller decrease in discharge intensity.

In this embodiment, in which the thin light-emitting layers 41 are disposed in the regions directly above the electrodes 7, the discharge onset voltage is more affected by the secondary electron emission characteristics of the layer below the first light-emitting layers 41. It is therefore effective to provide the protective layer 5 below the first light-emitting layers 41, as shown in FIG. 11. The protective layer 5 may be made of a material with good secondary electron emission characteristics and high ion bombardment resistance. For example, the use of a thin MgO film, which is stable and has high ion bombardment resistance, provides an ultraviolet light-emitting device that exhibits only a minimal change in discharge intensity over time and has high luminous intensity.

Figure 12:
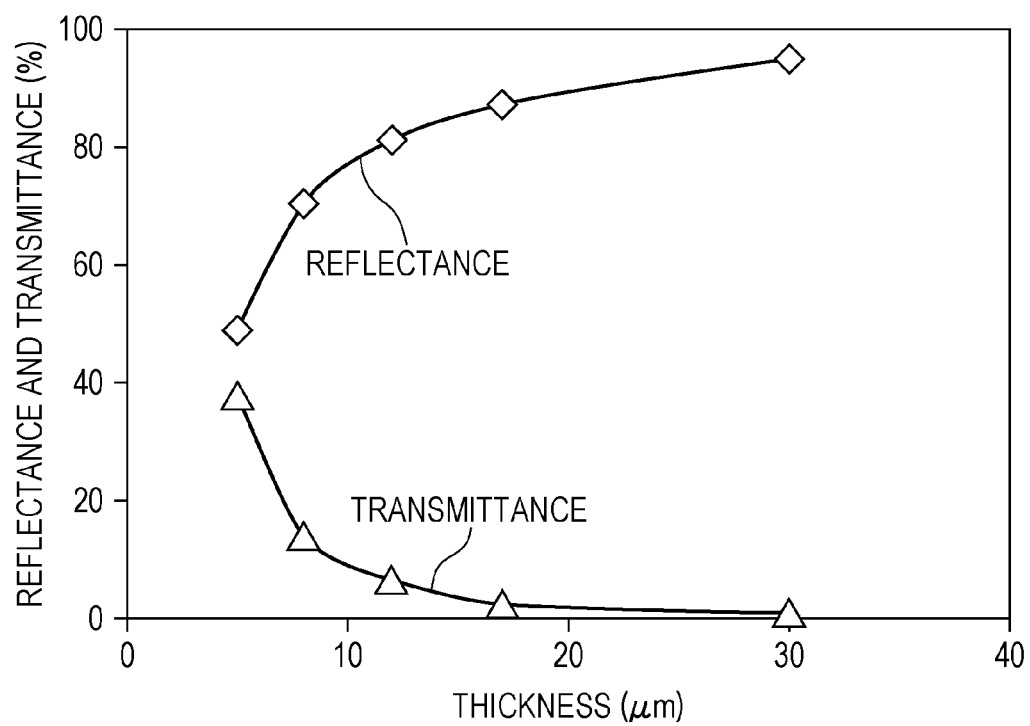
FIG. 12 is a graph showing the relationship between the transmittance and reflectance and the thickness of a light-emitting layer.

If a powder of a light-emitting material is used for the first light-emitting layers 41, the first light-emitting layers 41 in the regions directly above the electrodes 7 may have a thickness of less than 10 μm. FIG. 12 is a graph showing the thickness dependence of transmittance and reflectance observed when MgO powder is used for the light-emitting layer 40. The graph in FIG. 12 shows that the transmittance rises sharply below a thickness of 10 μm. If the first light-emitting layers 41 has a thickness of 10 μm or less, some of the ultraviolet light emitted from the surface of the first light-emitting layers 41 travels through the first light-emitting layers 41 toward the electrodes 7 and is absorbed by the dielectric layer 6. This reduces the proportion of the luminous intensity in the regions directly above the electrodes 7 to the luminous intensity of the ultraviolet light-emitting device 31$b$.

The first and second light-emitting layers 41 and 42 may be formed using a mask. Specifically, a light-emitting layer having the same thickness as the first light-emitting layers 41 is first formed over the entire protective layer 5. A mask is then formed in the first regions 46. The second light-emitting layers 42 are formed in the second regions 47 through the mask. Finally, the mask is removed.

Although the protective layer 5 is provided, as described above, it is optional and may be omitted. Although the first regions 46 in FIG. 11 have the same shape as the electrodes 7 in plan view, the first regions 46 may be wider or narrower than the electrodes 7. The first light-emitting layers 41 may be omitted in the first regions 46, and the protective layer 5 or the dielectric layer 6 may be exposed in the discharge space 10. This results in an even smaller decrease in the luminous intensity of the ultraviolet light-emitting device 31$b$ over time. In addition, the dielectric layer 6 and the protective layer 5 may be omitted in the second regions 47, and the second light-emitting layers 42 may be in direct contact with the first substrate 2. If the first substrate 2 transmits ultraviolet light, ultraviolet light can be output from both surfaces of the ultraviolet light-emitting device 31$b$. In this case, the ultraviolet irradiation apparatus 201 may further include a cyclone structure 33 and an ultraviolet light filter 32 disposed on the second main surface of the first substrate 2.

Although ultraviolet irradiation apparatuses according to one or more aspects have been described with reference to the first to third embodiments and the modifications thereof, these embodiments and modifications are not intended to limit the present disclosure. It should be appreciated that various modifications that can be made to the foregoing embodiments and modifications by those skilled in the art and various combinations of elements of different embodiments and modifications may be included in one or more aspects without departing from the spirit of the present disclosure. For example, the ultraviolet irradiation apparatuses 90 and 201 according to the second and third embodiments may include the second substrate 3$a$ according to the modification of the first embodiment instead of the second substrate 3 and the ultraviolet light filter 32. The ultraviolet irradiation apparatus 90 according to the second embodiment may include the deep-ultraviolet light-emitting device 31$b$ according to the third embodiment instead of the deep-ultraviolet light-emitting device 31.

Although a mixture of neon (Ne) and xenon (Xe) is used as a discharge gas in the first to third embodiments and the modifications thereof, other gases may be used, including xenon (Xe) alone and rare gas halides such as krypton chloride (KrCl).

In the first to third embodiments, the ultraviolet light filter 32 is optional and may be omitted. The ultraviolet light source used in the foregoing embodiments is the light-emitting layer 4, which emits deep-ultraviolet light in response to excitation light generated in the discharge space 10. Even if the ultraviolet irradiation apparatuses according to the foregoing embodiments include no ultraviolet light filter 32, they emit less light with wavelengths around 185 nm than those including mercury lamps, as indicated by the curve for "no ultraviolet light filter" in the graph in FIG. 6. These ultraviolet irradiation apparatuses therefore generate less ozone, which is harmful to humans. That is, even if the ultraviolet irradiation apparatuses according to the foregoing embodiments include no ultraviolet light filter 32, they can irradiate a fluid with ultraviolet light more efficiently while generating less ozone than those including mercury lamps.

In the first to third embodiments and the modifications thereof, the tubular structure 14 and the interior thereof are formed in a quadrangular prism shape that is square in plan view; however, they may be formed in other shapes. For example, the tubular structure 14 and the interior thereof may be formed in a quadrangular prism shape that is rectangular or has other quadrangular shapes in plan view. The tubular structure 14 and the interior thereof may also be formed in other polygonal prism shapes that have other polygonal shapes in plan view. The tubular structure 14 and the interior thereof may also be formed in a cylindrical shape that is circular or oval in plan view. As used herein, the term "polygon" refers to a shape with three or more sides. As used herein, the terms "square", "rectangular", "quadrangular", and "polygonal" encompass squares, rectangles, quadrangles, and polygons with rounded corners. As used herein, the terms "quadrangular prism" and "polygonal prism" encompass quadrangular prisms and polygonal prisms with rounded corners.

The present disclosure provides an ultraviolet irradiation apparatus that can efficiently irradiate a fluid with ultraviolet light while generating less ozone. Such an ultraviolet irradiation apparatus is useful, for example, as a processing apparatus for decomposing organic substances with deep-ultraviolet light, specifically, as a processing apparatus used in applications such as sterilization, deodorization, cleaning, water purification, lithography, and illumination.

What is claimed is:

1. An ultraviolet irradiation apparatus comprising:
   a first substrate having a main surface;
   a second substrate facing the main surface of the first substrate and comprising a material that transmits ultraviolet light;
   electrodes disposed directly or indirectly on the main surface of the first substrate;
   a dielectric layer covering the electrodes;
   a sealant joining together the first and second substrates to form a sealed discharge space between the first and second substrates;
   a light-emitting layer that is disposed directly or indirectly on the dielectric layer and/or a surface of the second substrate facing the discharge space and that receives excitation light generated in the discharge space and emits ultraviolet light; and
   a reaction vessel disposed directly or indirectly on a surface of the second substrate facing away from the discharge space,
   the reaction vessel comprising a tubular structure, an inlet channel that directs a fluid flowing from outside the reaction vessel into the tubular structure, and an outlet channel that directs the fluid flowing from inside the tubular structure out of the reaction vessel,
   the tubular structure having a ratio ha/hc of 5 to 10, wherein ha is a diameter of a circle inscribed in an inner bottom surface of the tubular structure, and hc is an inner height of the tubular structure.

2. The ultraviolet irradiation apparatus according to claim 1, wherein the inlet channel and the outlet channel are arranged at two opposite corners with respect to the center of the tubular structure.

3. The ultraviolet irradiation apparatus according to claim 1, wherein the tubular structure swirls the fluid directed into the tubular structure by the inlet channel, and
   the reaction vessel further comprises a tapered structure that directs the fluid swirling in the tubular structure into the outlet channel.

4. The ultraviolet irradiation apparatus according to claim 3, wherein the tubular structure is a prismatic tubular structure having curved inner walls at corners thereof.

5. The ultraviolet irradiation apparatus according to claim 3, further comprising an ultraviolet light filter that is disposed between the second substrate and the reaction vessel and that absorbs or reflects 80% or more of light with a wavelength of 200 nm or less.

6. The ultraviolet irradiation apparatus according to claim 3, wherein the second substrate is an ultraviolet light filter that absorbs or reflects 80% or more of light with a wavelength of 200 nm or less.

7. The ultraviolet irradiation apparatus according to claim 3, wherein the light-emitting layer comprises a magnesium oxide powder having an emission intensity peak between 200 and 300 nm.

8. The ultraviolet irradiation apparatus according to claim 3, wherein the light-emitting layer is disposed directly or indirectly on a surface of the dielectric layer facing the discharge space.

* * * * *